(12) United States Patent
Jasserand et al.

(10) Patent No.: US 7,767,692 B2
(45) Date of Patent: Aug. 3, 2010

(54) 1-AMIDOMETHYLCARBONYL-PIPERIDINE COMPOUNDS, METHODS AND INTERMEDIATE PRODUCTS FOR THE PRODUCTION THEREOF AND PHARMACEUTICAL FORMULATIONS CONTAINING SAID COMPOUNDS

(75) Inventors: Daniel Jasserand, Hannover (DE); Jochen Antel, Bad Muender (DE); Ulf Preuschoff, Isernhagen N.B. (DE); Reinhard Brueckner, Hannover (DE); Holger Sann, Hannover (DE); Michael Wurl, Garbsen (DE); Peter Eickelmann, Mittelbiberach (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 1875 days.

(21) Appl. No.: 10/704,356

(22) Filed: Nov. 10, 2003

(65) Prior Publication Data

US 2004/0152732 A1 Aug. 5, 2004

Related U.S. Application Data

(63) Continuation of application No. PCT/EP02/04904, filed on May 4, 2002.

(60) Provisional application No. 60/291,935, filed on May 21, 2001.

(30) Foreign Application Priority Data

May 10, 2001 (DE) ................................ 101 22 603

(51) Int. Cl.
*A61K 31/445* (2006.01)
*C07D 211/00* (2006.01)
*C07D 405/00* (2006.01)
*C07D 211/06* (2006.01)
*C07D 211/56* (2006.01)

(52) U.S. Cl. ........................ 514/315; 514/317; 514/319; 514/320; 514/323; 546/184; 546/192; 546/195; 546/196; 546/200; 546/244; 546/248

(58) Field of Classification Search ................ 514/691, 514/729, 766, 315, 317, 319, 320, 323; 546/184, 546/192, 195, 196, 200, 244, 248
See application file for complete search history.

(56) References Cited

U.S. PATENT DOCUMENTS 5,418,224 A 5/1995 Hoeltje et al.
6,277,877 B1 * 8/2001 Hoover et al. ................ 514/415

FOREIGN PATENT DOCUMENTS

| EP | 0 076 530 A2 | | 4/1983 |
|---|---|---|---|
| EP | 0550895 | | 7/1993 |
| FR | 2914923 | * | 4/2007 |
| GB | 2 351 733 A | | 1/2001 |
| WO | WO 96/39384 A1 | | 12/1996 |
| WO | WO 99/09991 A1 | | 3/1999 |
| WO | WO 00/74679 A1 | | 12/2000 |
| WO | WO 2008116816 | * | 10/2008 |
| WO | WO 2008122378 | * | 10/2008 |

OTHER PUBLICATIONS

Maistrello et al. (Effects of nootkatone and a borate compound on Formosan substerrean termite and its symbiont protozoa, J. of Entomological Science, 2001, 36(3), 229-6).*
A. R. Jacobson et al., "Minimum-Strucutre Enkephalin Analogues Incorporating L-Tyrosine, D(or L)-Pehnylanine, and a Diamine Spacer" *J. Med. Chem.*, 1989, 32, pp. 1708-1717.

* cited by examiner

*Primary Examiner*—Alton N Pryor
(74) *Attorney, Agent, or Firm*—Crowell & Moring LLP

(57) ABSTRACT

4-substituted 1-amidomethylcarbonyl-piperidine compounds having motilin-agonistic properties and their acid addition salts, pharmaceutical compositions containing these compounds, processes and intermediate products for the preparation of these compounds, and methods of treatment utilizing these compounds.

40 Claims, No Drawings

1-AMIDOMETHYLCARBONYL-PIPERIDINE COMPOUNDS, METHODS AND INTERMEDIATE PRODUCTS FOR THE PRODUCTION THEREOF AND PHARMACEUTICAL FORMULATIONS CONTAINING SAID COMPOUNDS

CROSS-REFERENCE TO RELATED APPLICATIONS

This application is a continuation of International Patent Application PCT/EP02/04904, filed May 4, 2002, designating the United States of America and published in German as WO 02/092592, the entire disclosure of which is incorporated herein by reference. Priority is claimed based on Federal Republic of Germany Patent Application No. DE 101 22 603.9, filed May 10, 2001 and U.S. Provisional Application No. 60/291,935, filed May 21, 2001.

FIELD OF THE INVENTION

The present invention relates to novel, 4-substituted 1-amidomethylcarbonyl-piperidine compounds having motilin-agonistic properties and their acid addition salts, and to pharmaceutical preparations containing these compounds and processes and intermediate products for the preparation of these compounds.

BACKGROUND OF THE INVENTION

Motilin-agonistic compounds having macrolidic structures are already known, for example, from European Patent EP 0 550 895 B1.

Inter alia, 1,4-substituted piperidine compounds are already known from International Patent Application WO 97/38665 which are effective as inhibitors of farnesyl protein transferase.

SUMMARY OF THE INVENTION

It is an object of the present invention to provide novel compounds having a beneficial effect on the motility of the gastrointestinal tract, in particular having a motilin-like effect, which do not have a macrocyclic basic structure derived from erythromycin.

It has now surprisingly been discovered that novel 1-amidomethylcarbonyl-piperidine compounds have selective motilin-agonistic properties and thus appear suitable to stimulate the motility of the gastrointestinal tract beneficially and to enhance the tone of the lower esophagus sphincter. Because of their activity profile, the compounds according to the invention therefore appear suitable for the treatment of motility disturbances in the gastrointestinal tract.

The invention thus relates to novel 1-amidomethylcarbonyl-piperidine compounds corresponding to Formula I,

I wherein
$R^1$ is phenyl-$C_{0-4}$-alkyl, which is optionally substituted in the phenyl ring by lower alkylenedioxy or 1 to 3 times by halogen, trifluoromethyl, lower alkyl or lower alkoxy,
heteroaryl-$C_{0-4}$-alkyl, which is optionally substituted in the heteroaryl ring by halogen, lower alkyl or lower alkoxy,
$C_{1-6}$-alkyl, which is optionally substituted by carboxy, hydroxy, oxo, hydroximino, lower alkyloximino, amino, lower alkylamino, di-lower alkylamino or lower alkoxy, or
$C_{3-6}$-cycloalkyl,
$R^2$ is $C_{1-8}$-alkyl,
naphthyl lower alkyl,
fluorenyl lower alkyl or
phenyl-$C_{0-4}$-alkyl, which is optionally substituted in the phenyl ring by lower alkylenedioxy or 1 to 3 times by trifluoromethyl, lower alkyl, di-lower alkylamino, lower alkoxy or phenyl-$C_{0-4}$-alkoxy which is optionally substituted in the phenyl ring by lower alkyl, lower alkoxy and/or lower alkylenedioxy,
$R^3$ is hydrogen,
lower alkyl,
naphthyl lower alkyl,
fluorenyl lower alkyl or
phenyl-$C_{0-4}$-alkyl, which is optionally substituted in the phenyl ring by lower alkylenedioxy or 1 to 2 times by lower alkyl, di-lower alkylamino, lower alkoxy or phenyl-$C_{0-4}$-alkoxy which is optionally substituted in the phenyl ring by lower alkyl or lower alkoxy,
Ar is phenyl, which is optionally substituted by lower alkylenedioxy or 1 to 3 times by halogen, lower alkyl or lower alkoxy,
naphthyl, which is optionally substituted by lower alkylenedioxy or 1 to 3 times by halogen, lower alkyl or lower alkoxy, or
indolyl, which is optionally substituted by halogen, lower alkyl or lower alkoxy,
and
n is a whole number between 0 and 3, and their stable, physiologically compatible acid addition salts.

Where the substituents in the compounds of Formula I are or contain lower alkyl groups, these may be straight-chain or branched and contain 1 to 4 carbon atoms. Where the substituents contain halogen, in particular fluorine, chlorine or bromine, preferably fluorine or chlorine, are used. Where substituents in the compounds of Formula I contain phenyl substituted by lower alkylenedioxy, lower alkylenedioxy is preferably oxygen atoms bonded to two adjacent atoms of the phenyl ring, which are bridged via a lower-alkylene chain with 1 to 4, in particular 1 to 2, carbon atoms. In one embodiment, lower alkylenedioxy is methylenedioxy.

Preferably, $R^1$ is phenyl-$C_{0-4}$-alkyl. In a particularly preferred variant, $R^1$ is phenylethyl. Where $R^1$ is heteroaryl-$C_{0-4}$-alkyl, electron-rich heteroaryl radicals are particularly suitable, for example furan, benzofuran, thiophene, benzothiophene, pyrrole or indole. Where $R^1$ is for $C_{1-6}$-alkyl, it is preferably substituted by at least one of the functional groups named above with reference to FIG. 1.

$R^2$ is preferably fluorenyl lower alkyl, in particular 2-fluorenylmethyl, or phenyl-$C_{0-4}$-alkyl, which is preferably substituted. In a preferred variant, $R^2$ is phenyl-$C_{0-4}$-alkyl substituted in the 3,4 position of the phenyl ring by methylenedioxy. In another preferred variant, $R^2$ is phenylmethyl, which is substituted in the phenyl ring by lower alkoxy, in particular methoxy, and by phenyl-$C_{0-4}$-alkoxy optionally substituted by lower alkyl, in particular benzyloxy.

$R^3$ is preferably hydrogen or lower alkyl. Hydrogen is preferred.

Ar is preferably indolyl, either substituted or unsubstituted. Unsubstituted indolyl is preferred. Where Ar is substituted, phenyl, 3,4-dichlorophenyl is preferred.

A method for treatment or prophylaxis of pathological conditions in a mammal which are associated with motility disturbances in the gastrointestinal tract or reflux of chyme from the stomach into the esophagus comprising administering to said mammal a pharmaceutically effective amount of a compound corresponding to Formula I is provided in accordance with one embodiment of the invention.

The compounds of Formula I and their acid addition salts may be prepared as follows:

a) for the preparation of a compound corresponding to Formula Ia,

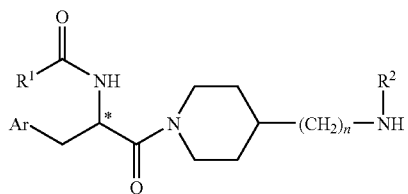

Ia wherein $R^1$, $R^2$, Ar and n have the above meanings, a compound corresponding to Formula II,

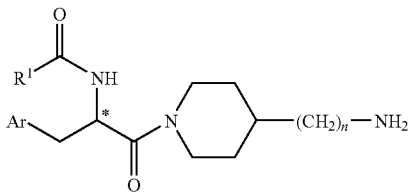

II wherein $R^1$, Ar and n have the above meanings and wherein optionally present functional groups which are reactive under the reaction conditions are blocked with suitable protective groups, is reacted with a compound corresponding to Formula III,

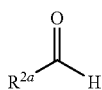

III wherein $R^{2a}$ has the same meaning as $R^2$ except that the alkylene chain has less alkylene group, and wherein optionally present functional groups which are reactive under the reaction conditions are blocked with suitable protective groups, under conditions of reductive amination and unwanted protective groups are subsequently cleaved again, or b) for the preparation of compounds corresponding to Formula Ib

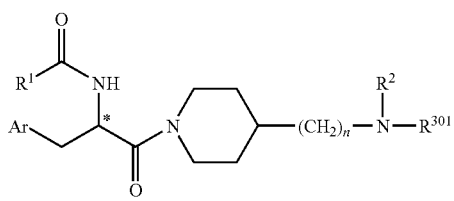

Ib wherein $R^1$, $R^2$, Ar and n have the above meanings and $R^{301}$ has the meaning given above for $R^3$ with the exception of hydrogen, a compound of Formula Ia, wherein optionally present functional groups which are reactive under the reaction conditions are blocked with suitable protective groups, is reacted with a compound corresponding to Formula IV

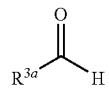

IV wherein $R^{3a}$ has the same meaning as $R^{301}$ except that the alkylene chain has one less alkylene group, and wherein optionally present functional groups which are reactive under the reaction conditions are blocked with suitable protective groups, under conditions of reductive amination and unwanted protective groups are subsequently cleaved again, and free compounds of Formula I if desired are converted into their acid addition salts or acid addition salts of the compounds of Formula I are converted into free compounds.

According to process variant a), a primary amine of Formula II can be reacted with an aldehyde of Formula III in the presence of a suitable reducing agent in known manner under conditions of reductive amination, in order to obtain a compound of Formula Ia. The reaction may take place in a solvent which is inert under the reaction conditions, preferably at temperatures between −20° C. and room temperature. Suitable solvents are for example halogenated hydrocarbons such as dichloromethane or cyclic ethers such as tetrahydrofuran (THF) or dioxane or mixtures of these solvents. Suitable reducing agents are complex alkali metal borohydrides, in particular sodium triacetoxy borohydride. Protective groups which are suitable for the selective introduction and subsequent selective cleaving in the above process variant a) and in the preparation processes referred to below are known per se, for example from J. A. W. McOmie "Protective Groups in Organic Chemistry", Plenum Press, or from T. W. Green and P. G. M. Wuts "Protective Groups in Organic Synthesis", Wiley and Sons, 1991. A person of skill in the art can select suitable protective groups for each case by routine methods.

According to process variant b), a secondary amine of Formula Ia can be reacted with an aldehyde of Formula IV in the presence of a suitable reducing agent in known manner under conditions of reductive amination, in order to obtain a compound of Formula Ib. The reaction may take place, for example, in the manner described above for the reaction of compounds of Formula II with compounds of Formula III.

Compounds of Formula II and their stereoisomeric forms are novel compounds which are suitable as intermediate products for the preparation of novel pharmacologically active substances, for example for the preparation of the compounds of Formula I. The compounds of Formula II can be prepared by reacting compounds corresponding to Formula V,

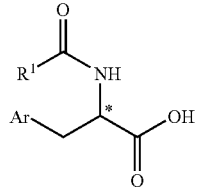

V wherein $R^1$ and Ar have the above meanings and wherein optionally present functional groups which are reactive under the reaction conditions are each blocked with suitable protective groups, with compounds corresponding to Formula VIa,

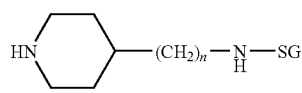

VIa wherein n has the above meaning and SG stands for an amino protective group which is stable under the reaction conditions, and unwanted protective groups are subsequently cleaved again. The reaction of the acids of Formula V with the piperidine compounds of Formula VIa to form the amides of Formula II can be carried out according to conventional methods for the formation of amide groups by aminoacylation. The acids of Formula V or their reactive compounds such as acid halides or mixed anhydrides of the acids of Formula V with sulfuric acids such as toluene sulfonates of the acids of Formula V may be used as acylation agents. The acylation may take place in an organic solvent which is inert under the reaction conditions, preferably at temperatures between –20° C. and room temperature. Suitable solvents are in particular halogenated hydrocarbons such as dichloromethane or cyclic ethers such as THF or dioxane or mixtures of these solvents. The acylation may be expediently carried out in the presence of an acid-binding agent. Suitable acid-binding agents are bases soluble in the reaction mixture, in particular organic bases such as tertiary lower alkylamines and pyridines, for example triethylamine, tripropylamine or 4-dimethylaminopyridine. If the acids of Formula V themselves are used as acylation agents, the acylation can also be expediently performed in the presence of coupling reagents known from peptide chemistry to be suitable for amide formation, such as alkyl carbodiimides, e.g. dicyclohexyl carbodiimide or carbonyl diimidazole.

Compounds of Formula V can be prepared by reacting compounds corresponding to Formula VII,

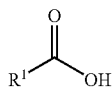

VII wherein $R^1$ has the above meaning and wherein optionally present functional groups which are reactive under the reaction conditions are each blocked with suitable protective groups, with compounds corresponding to Formula VIII,

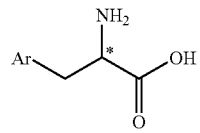

VIII wherein Ar has the above meaning. The reaction can be carried out according to conventional methods for the formation of amide groups by aminoacylation, for example in the manner given above for the reaction of compounds of Formula V with compounds of Formula VIa.

The acids of Formula VII are known or can be prepared by persons skilled in the art from known compounds by routine chemical methods.

The α-aminocarboxylic acids of Formula VIII are known, or can be prepared by persons skilled in the art from known compounds by routine chemical methods.

The compounds of Formula VIa can be prepared by introducing suitable protective groups SG from the compounds corresponding to Formula VI,

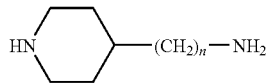

VI wherein n has the above meaning. Suitable protective groups SG are in particular protective groups known from peptide chemistry, preferably the tert. butyloxycarbonyl protective group ($^t$BOC).

The compounds of Formula VI are known or can be prepared by persons skilled in the art from known compounds by routine chemical methods.

The compounds of Formula I may be isolated from the reaction mixture and purified using conventional methods. Acid addition salts may be converted into the free bases in a conventional manner, and these may be converted into physiologically compatible acid addition salts using conventional methods.

Physiologically compatible salts of compounds of Formula I include their salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or benzenesulfonic acids optionally substituted in the benzene ring by halogen or lower alkyl, such as p-toluenesulfonic acid.

The compounds of Formula I contain a chiral carbon atom, namely the carbon atom marked "*" in position β relative to the ring nitrogen atom of the piperidine ring. Thus, the compounds of Formula I can be present in several stereoisomeric forms. The present invention covers both the mixtures of optical isomers and the isomerically pure compounds of Formula I. Compounds of Formula I, wherein the above chiral center is in the R configuration are preferred. If mixtures of optical isomers of the starting compounds, for example of the compounds of Formula II or the compounds of Formula VII, are used in the synthesis of the compounds of Formula I, the compounds of Formula I are also obtained in the form of mixtures of optical isomers. Departing from stereochemically uniform forms of the starting compound, stereochemically uniform compounds of Formula I can also be obtained. The stereochemically uniform compounds of Formula I can be obtained from the mixtures of optical isomers in a known manner, for example by chromatographic separation on chiral separating materials or by reaction with suitable optically active acids, for example tartaric acid or 10-camphorsulfonic acid, and subsequent separation into their optically active antipodes by fractional crystallization of the diastereomeric salts obtained.

The novel compounds of Formula I and their physiologically compatible acid addition salts have advantageous pharmacological properties, in particular motilin-agonistic properties which stimulate the motility of the gastrointestinal tract.

In the healthy state, the autonomic nervous system and hormones in the gastrointestinal tract cooperate to ensure controlled digestion of the consumed food, in order to generate a controlled contraction activity of the gastrointestinal tract not only immediately after intake of food but also when the gastrointestinal tract is empty. Motilin is a known gastrointestinal peptide hormone which stimulates the motility of the gastrointestinal tract and induces a coordinated motility throughout the gastrointestinal tract in the fasting state and after intake of food.

The compounds of Formula I exhibit motilin-like effects in that they act as agonists for motilin receptors. Thus, it is to be expected that the compounds of Formula I show pronounced stimulating effects in the gastrointestinal region and at the lower esophagus sphincter, or alternatively in other regions of the body which contain motilin receptors, for example in the CNS. Furthermore, it is to be expected that the compounds of Formula I bring about an increased rate of gastric emptying. Because of their motilin-like method of action, the substances appear suitable for the treatment of conditions which are associated with motility disturbances in the gastrointestinal tract and/or reflux of chyme from the stomach into the esophagus. Thus, the compounds of Formula I are indicated, for example, for gastroparesis with a wide variety of causes, for example diabetic gastroparesis, disturbances of gastric emptying and gastroesophageal reflux, dyspepsia, anomalies in colon motility such as occur e.g. in irritable bowel syndrome (IBS) and postoperative motility disturbances, e.g. intestinal blockage (ileus) or also in the cases of disturbances in emptying of the gall bladder.

The gastrointestinally effective properties of the compounds of Formula I can be demonstrated in standard pharmacological test methods.

Description of the pharmacological test methods

The motilin-agonistic actions of the test substances may for example be demonstrated in a standard pharmacological test in vitro.

For this, Chinese hamster ovary cells (CHO cells) were each transfected in known manner with an expression vector for the human motilin receptor GPR38 (cf. K. K. McGee et al., Genomics 46 (1997) 426-434) and for apoaequorin (cf. EP 0 187 519 B1 or U.S. Pat. No. 5,162,227; U.S. Pat. No. 5,422,266; U.S. Pat. No. 5,744,579; U.S. Pat. No. 5,766,941 and U.S. Pat. No. 5,798,441).

The cDNA for the motilin-receptor (GPR38) was obtained from cDNA from human stomach tissue by polymerase chain reaction (PCR) with suitable oligonucleotides as primers. The cloning of the PCR product initially took place into the cloning vector pCR-blunt (from INVITROGEN). The cloned sequence was confirmed by DNA sequencing. Then the cDNA was subcloned using the restriction endonucleases HindIII and SpeI into suitable restriction enzyme cutting sites (HindIII, Xba I) of the expression vector pcDNA3 (from INVITROGEN, NL). The cDNA for mitochondrially expressed aequorin was cut out from the plasmid mtAEQ/pMT2 (from Molecular Probes, catalog number A-6788) by restriction enzymes and was subcloned into the expression vector pIRES-puro (from CLONTECH, catalog number 6031-1). Selection for the presence of the two expression constructs in the transfected CHO cells was effected with G418 and puromycin. The cell culture was effected in DMEM/F12 (1:1) Medium (cf. LIFE TECHNOLOGIES catalog No. 11039-02, composition of the media described in: Dulbecco et al. Virology 8 (1959) 396; Smith et al. Virology 12 (1960) 185; Tissue Culture Standards Committee, In Vitro 6:2, 93rd Ham (1965) Proc. Natl. Acad. Sci., 53, 288) with 10% (V/V) fetal calf serum, 100 IU/ml penicillin, 100 µg/ml streptomycin, 5 µg/ml puromycin and 400 µg/ml G418.

The motilin receptor is coupled via G-proteins to the $Ca^{2+}$-signal transduction path of the CHO cell, i.e. activation of the receptor leads to a transient increase in the intracellular $Ca^{2+}$ concentration. The aequorin resulting from loading the apoaequorin-expressing CHO cells with coelenterazine can react with the mitochondrial $Ca^{2+}$ ions of the CHO cells, releasing chemiluminescence. The chemiluminescence released is proportional to the concentration of the motilin-agonistic compounds of Formula I which are used. In the present test model, the compounds of Formula I are measured in constant concentrations. The measured chemiluminescence is therefore a measurement of the effectiveness of the test compounds as motilin agonists.

The pharmacological test is performed in accordance with a process known from WO 00/02045.

CHO cells transfected with the GPR38 receptor in their logarithmic growth phase were detached from their culture dishes with phosphate-buffered common salt solution which was free of $Ca^{2+}$ ions, which contained an addition of 5 mM ethylenediamine tetraacetate (PBS-EDTA) solution and were centrifuged, and the supernatant was discarded. The remaining pellets were resuspended in a BSA medium [DMEM/F12 (1:1) medium with HEPES (15 M), 0.1% bovine serum albumin (BSA), 100 IU/ml penicillin, 100 µg/ml streptomycin, without phenol red]. Then the cells were counted in a Neubauer chamber, centrifuged again and resuspended in the above BSA medium, so that the cell density was $5 \times 10^6$-cells/ml. A 500 µM stock solution of coelenterazine h in methanol was added until a final concentration of 5 µM was reached in the BSA medium. The cells were kept in suspension in a glass beaker wound around with aluminum foil on a magnetic stirrer by slow stirring, and were incubated for a total of 4 hours at room temperature in order to obtain active aequorin. Then the cells were diluted once again to 10 times the volume with the aforementioned BSA medium and stirred for 30 minutes at room temperature. Solutions of a reference agonist (motilin in a concentration of $10^{-7}$ M was used as reference agonist) and test compounds (1% in DMSO) were placed in the wells of a sample plate with 96 sample places (96-well plate) (10 µl each). 90 µl of the cell suspension prepared above (i.e. 45,000 cells) was added in each case via pipette to this receiving solution via the injector of a MicrobetaJet (from WALLAC) and the light emitted was measured over 15 seconds and integrated. In this manner, a representative value for each well was obtained for the emitted light and accordingly for the intensity of the stimulation of the motilin receptor by the compound of Formula I present in the corresponding well.

For the compounds of the examples below, the intensity of the stimulation of the human motilin receptor GPR38 was determined in each case by a single measurement of the test substances in a concentration of $10^{-5}$ M. All the test substances of Examples 1 to 16 in this test model exhibited stimulation of the human GPR38 motilin receptor, which was at least 40% of the stimulation of this receptor by the reference agonist motilin. The compounds of Examples 6 to 16 each exhibited stimulation of at least 60%, relative to the stimulation by the reference agonist motilin. The example numbers quoted relate to the following preparation examples.

The compounds of Formula I may be administered in conventional pharmaceutical preparations. The doses to be used may vary individually and will naturally vary according to the type of condition to be treated and the substance used. In general, however, medicinal forms with an active substance content of 0.1 to 800 mg, in particular 1 to 100 mg, active substance per individual dose are suitable for administration to humans and larger mammals.

The compounds may be provided together with conventional pharmaceutical auxiliaries and/or carriers, in solid or liquid pharmaceutical preparations. Examples of solid preparations are preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or carriers in known manner. For the production of solid medicament forms, the active substances may, for example, be mixed with the auxiliaries and/or carriers in conventional manner and may be wet or dry granulated. The granules or powder can be poured directly into capsules or be pressed into tablet cores in a conventional manner. These can be coated in known manner, if desired.

The following examples are provided to further explain and clarify certain embodiments of the invention. These examples are not intended to, and they should not be interpreted to, limit the scope of the appended claims.

EXAMPLE 1

N-[(1RS)-2-({[3-(1,3-benzodioxol-5-yl)-((2RS)-methylpropyl]amino}-1-piperidinyl)-1-(1H-indol-3-ylmethyl)-2-oxoethyl]-3-phenylpropanamide A) 15.0 g NaOH was dissolved in 150 ml water and 51.0 g DL-Tryptophan was added. Then, a solution of 37.0 ml 3-phenylpropionic acid chloride in 75 ml THF was added to this receiving solution with stirring and ice cooling. After further stirring for 45 minutes at room temperature, the pH of the reaction solution was set to 3-4 by dropwise addition of concentrated HCl. The white solid obtained after the addition of water was separated by vacuum filtration. 59.8 g DL-N-phenylpropionyltryptophan was obtained with a melting point (mp.) of 175-176° C.

B) 3.4 g of the tryptophan compound obtained above was dissolved at room temperature and under a protective gas atmosphere in 200 ml THF, 1.7 g carbonyl diimidazole was added thereto and the mixture stirred for 1 hour at room temperature. Then a solution of 2.0 g 4-(tert. butyloxycarbonylamino)piperidine in 25 ml dichloromethane was added dropwise to this receiving solution, stirring was continued for one hour at room temperature and then the reaction mixture was left to stand overnight. Then excess THF was evaporated in a vacuum and the residue was taken up in 200 ml ethyl acetate. The organic phase was treated in succession 2 times with 50 ml water, once with 15 ml 15% strength aqueous tartaric acid solution, 3 times with 50 ml water, once with 50 ml dilute aqueous potassium carbonate solution and finally washed twice with 50 ml water. The organic phase was then dried over sodium sulfate and evaporated to dryness. 4.5 g N-[3-phenylpropionyl]-DL-tryptophan-(4-(tert.-butoxycarbonyl)amino)piperidinamide was obtained as a white solid, with a melting point of 105-110° C.

C) The resulting product was combined from a plurality of batches from the reaction described above under B) to give a total of 25.0 g, and was suspended under a protective gas atmosphere in 800 ml methanol. 90 ml of a 37% strength aqueous HCl was added to this receiving solution with stirring and was left to stand overnight. The excess methanol was largely evaporated, the residue was taken up in 100 ml water and the aqueous phase was washed with ethyl acetate. The aqueous phase was separated and brought to a pH value of 8 by addition of dilute aqueous sodium hydroxide solution. The aqueous phase was extracted with approximately 100 ml ethyl acetate, the resulting precipitate was filtered and the organic phase was washed with saturated aqueous common salt solution. Then the organic phase was dried and the solvent was evaporated to dryness. 13.5 g N-[3-phenylpropionyl]-DL-tryptophan(4-amino)-piperidinamide was obtained as a white powder, which after chromatography (silica gel, mobile solvent: first dichloromethane, then dichloromethane/ethanol/triethylamine 90:7:3) and recrystallization from n-pentane, had a melting point of 70-73° C.

D) 400 mg of the product obtained above under C) was dissolved in 40 ml 1,2-dichloroethane at room temperature and under a protective gas atmosphere. 0.19 ml 3-(3,4-methylenedioxyphenyl)-2-methylpropanaldehyde and after a few minutes then 550 mg sodium triacetoxyborohydride were added to this receiving solution. It was stirred for 60 hours at room temperature and then washed with 30 ml saturated aqueous sodium hydrogen carbonate solution. The aqueous phase was extracted with 30 ml dichloromethane and the combined organic phases were dried over sodium sulfate. It was evaporated virtually to dryness and the remaining residue was purified by column chromatography (silica gel, mobile solvent: first ethyl acetate, to which gradually ethanol was admixed until a ratio of 9:1 was reached). Combination and drying of the product phases yielded 590 mg of the title compound (N-[(1RS)-2-({[3-(1,3-benzodioxol-5-yl)-((2RS)-methylpropyl]amino}-1-piperidinyl)-1-(1H-indol-3-ylmethyl)-2-oxoethyl]-3-phenylpropanamide) as a whitish solid.

E) 360 mg of the product base obtained above were dissolved at 50° C. in 15 ml methyl-tert. butylether. 0.5 ml of isopropanolic HCl was added to this receiving solution and it was stirred for 10 minutes at approximately 50° C. The reaction mixture was left to stand overnight at room temperature, the resulting solid was filtered and dried at 60° C. under vacuum. 350 mg of a hydrochloride of the title compound (N-[(1RS)-2-({[3-(1,3-benzodioxol-5-yl)-((2RS)-methylpropyl]amino}-1-piperidinyl)-1-(1H-indol-3-ylmethyl)-2-oxoethyl]-3-phenylpropanamide) was obtained, melting point of 124-127° C.

EXAMPLE 2

N-[(1R)-2-(4{[3-(1,3-benzodioxol-5-yl)-(2RS)-methylpropyl]amino}-1-piperidinyl)-1-(1H-indol-3-ylmethyl)-2-oxoethyl]-3-phenylpropanamide A) 30.28 g D-(−)-Tryptophan was reacted with 28.38 ml 3-phenylpropionic acid chloride in the manner indicated in Example 1A). 16.88 g D-N-phenylpropionyltryptophan was obtained as a white powder.

B) 5.13 g of the D-(−)-Tryptophan compound obtained above was reacted with 3.0 g 4-(tert. butoxycarbonylamino)piperidine in the manner indicated in Example 1B). 6.5 g N-[3-Phenylpropionyl-D-tryptophan-(4-(tert. butoxycarbonyl)amino)piperidinamide was obtained as a white solid, with a melting point of 105-110° C.

C) 6.2 g of the product obtained above was de-protected by the addition of 37% strength aqueous HCl in the manner indicated in Example 1C). 2.3 g N-[3-Phenylpropionyl]-D-tryptophan-(4-amino)-piperidinamide was obtained as a whitish foam.

D) 719 mg of the product obtained above was reacted with 0.33 ml 3-(3,4-methylenedioxyphenyl)-2-methylpropanaldehyde in the manner indicated in Example 1D). 670 mg of the title compound (N-[(1R)-2-(4{[3-(1,3-benzodioxol-5-yl)-(2RS)-methylpropyl]amino}-1-piperidinyl)-1-(1H-indol-3-ylmethyl)-2-oxoethyl]-3-phenylpropanamide) was obtained as a foam.

E) 630 mg of the title compound obtained above was converted into the hydrochloride in the manner indicated in Example 1E). 640 mg of a hydrochloride of the title compound (N-[(1R)-2-(4{[3-(1,3-benzodioxol-5-yl)-(2RS)-methylpropyl]amino}-1-piperidinyl)-1-(1H-indol-3-ylmethyl)-2-oxoethyl]-3-phenylpropanamide) was obtained, with a melting point of 140-145° C.; optical rotation $[\alpha]_D^{20} = 9.3°$ (c=1.0 in methanol).

The compounds of Examples 3 to 16 listed below can also be prepared according to the preparation processes described above or analogously to these preparation processes.

The following compounds of Examples 3 to 16 were prepared using an automated preparation process. Stock reagents of sodium triacetoxyborohydride (0.25 M suspension in chloroform) and of the aldehyde of Formula III, which was provided as reaction partner in each case (0.25 M in chloroform), were prepared. Thereupon, in each case, 200 μl racemic N-[3-phenylpropionyl]-tryptophan-(4-amino)-piperidinamide of Formula Ia (0.25 M in chloroform), 500 μl of the sodium acetoxyborohydride stock reagent and 200 μl of the aldehyde stock reagent were added to a micro-reaction vessel. The reaction vessel was closed and the reaction mixture was shaken overnight. The resulting crude products of compounds of Formula I were each diluted with 1.2 ml chloroform and extracted with 2.0 ml of a 1N aqueous NaOH. The supernatant phases were discarded and the lower phases were each washed with 2.0 ml water. The resulting lower phases were again transferred into micro-reaction vessels and the supernatant phases were each extracted once with chloroform. The combined organic phases were each evaporated virtually to dryness and the resulting residues were each taken up in 1.8 ml dimethyl sulfoxide (DMSO). Samples were each taken from the resulting DMSO solutions without further purification for high-performance liquid chromatography (HPLC) and for automatic mass spectroscopy to determine the purity and to confirm the structure.

All the compounds of Formula I listed in Table 1 below are of racemic configuration at the chiral center marked "*" in position β relative to the ring nitrogen atom of the piperidine ring.

TABLE 1

Further compounds of Formula I

| Ex. No. | $R^1$ | $R^2$ | $R^3$ | Ar | n |
|---|---|---|---|---|---|
| 3 | $H_5C_6-(CH_2)_2-$ | 1-naphthylmethyl | H | 3-indolyl | 0 |
| 4 | $H_5C_6-(CH_2)_2-$ | 2-naphthylmethyl | H | 3-indolyl | 0 |
| 5 | $H_5C_6-(CH_2)_2-$ | phenylpropyl | H | 3-indolyl | 0 |
| 6 | $H_5C_6-(CH_2)_2-$ | 4-isopropylbenzyl | H | 3-indolyl | 0 |
| 7 | $H_5C_6-(CH_2)_2-$ | 4-phenoxybenzyl | H | 3-indolyl | 0 |
| 8 | $H_5C_6-(CH_2)_2-$ | 4-dimethylaminobenzyl | H | 3-indolyl | 0 |
| 9 | $H_5C_6-(CH_2)_2-$ | 3-phenoxybenzyl | H | 3-indolyl | 0 |
| 10 | $H_5C_6-(CH_2)_2-$ | (3-methoxy-4-benzyloxy)-benzyl | H | 3-indolyl | 0 |
| 11 | $H_5C_6-(CH_2)_2-$ | 3-(4-tert.-butylphenoxy)-benzyl | H | 3-indolyl | 0 |
| 12 | $H_5C_6-(CH_2)_2-$ | 4-tert.-butylbenzyl | H | 3-indolyl | 0 |
| 13 | $H_5C_6-(CH_2)_2-$ | 2-fluorenylmethyl | H | 3-indolyl | 0 |
| 14 | $H_5C_6-(CH_2)_2-$ | 4-diethylaminobenzyl | H | 3-indolyl | 0 |
| 15 | $H_5C_6-(CH_2)_2-$ | n-$C_7H_{15}$ | H | 3-indolyl | 0 |
| 16 | 3,4-dichlorophenyl | 3-[(3,4-methylenedioxyphenyl)-2-methyl]-propyl | H | 3-indolyl | 0 |

EXAMPLE I

Capsules containing N-[(1R)-2-(4{[3-(1,3-benzodioxol-5-yl)-(2RS)-methylpropyl]amino}-1-piperidinyl)-1-(1H-indol-3-ylmethyl)-2-oxoethyl]-3-phenylpropanamide:

Capsules with the following composition per capsule were produced:

| | |
|---|---|
| N-[(1R)-2-(4{[3-(1,3-benzodioxol-5-yl)-(2RS)-methylpropyl]amino}-1-piperidinyl)-1-(1H-indol-3-ylmethyl)-2-oxoethyl]-3-phenylpropanamide | 20 mg |
| Corn starch | 60 mg |
| Lactose | 300 mg |
| Ethyl acetate | q.s. |

The active substance, the corn starch and the lactose were processed into a homogenous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 9 mg | and then poured into 400 mg capsules (capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for treating a pathological condition in a mammal associated with motility disturbances in the gastrointestinal tract or with reflux of chyme from the stomach into the esophagus in a mammal in need thereof, said method comprising administering to said mammal a pharmaceutically effective amount of a compound corresponding to Formula I wherein

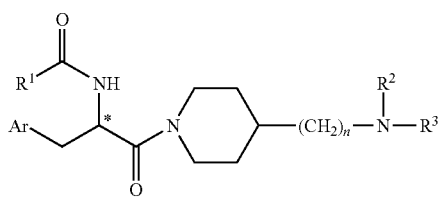

I $R^1$ is optionally substituted phenyl-$C_{0-4}$-alkyl,
optionally substituted heteroaryl-$C_{0-4}$-alkyl, wherein said heteroaryl is selected from the group consisting of furan, benzofuran, thiophene, benzothiophene and pyrrole;
optionally substituted $C_{1-6}$-alkyl, or
$C_{3-6}$-cycloalkyl;
$R^2$ is $C_{1-8}$-alkyl,
naphthyl lower alkyl,
fluorenyl lower alkyl, or
optionally substituted phenyl-$C_{0-4}$-alkyl;
$R^3$ is hydrogen,
lower alkyl,
naphthyl lower alkyl,
fluorenyl lower alkyl, or
optionally substituted phenyl-$C_{0-4}$-alkyl;
Ar is optionally substituted phenyl,
optionally substituted naphthyl, or
optionally substituted indolyl; and
n is a whole number between 0 and 3,
or a salt thereof with a physiologically tolerated acid.

2. The method of claim 1, wherein $R^1$ is phenyl-$C_{0-4}$-alkyl which is substituted in the phenyl ring by lower alkylenedioxy or is substituted 1 to 3 times by halogen, trifluoromethyl, lower alkyl or lower alkoxy.

3. The method of claim 1, wherein $R^1$ is heteroaryl-$C_{0-4}$-alkyl, which is substituted in the heteroaryl ring by halogen, lower alkyl or lower alkoxy.

4. The method of claim 1, wherein $R^1$ is $C_{1-6}$-alkyl, which is substituted by carboxy, hydroxy, oxo, hydroximino, lower alkyloximino, amino, lower alkylamino, di-lower alkylamino or lower alkoxy.

5. The method of claim 1, wherein $R^2$ is phenyl-$C_{0-4}$-alkyl, which is substituted in the phenyl ring by lower alkylenedioxy or is substituted 1 to 3 times by trifluoromethyl, lower alkyl, di-lower alkylamino, lower alkoxy or phenyl-$C_{0-4}$-alkoxy.

6. The method of claim 1, wherein $R^2$ is phenyl-$C_{0-4}$-alkyl, which is substituted in the phenyl ring by phenyl-$C_{0-4}$-alkoxy, which in turn is substituted in the phenyl ring by lower alkyl, lower alkoxy or lower alkylenedioxy.

7. The method of claim 1, wherein $R^3$ is phenyl-$C_{0-4}$-alkyl, which is substituted in the phenyl ring by lower alkylenedioxy or is substituted 1 to 2 times by lower alkyl, di-lower alkylamino, lower alkoxy or phenyl-$C_{0-4}$-alkoxy.

8. The method of claim 1, wherein $R^3$ is phenyl-$C_{0-4}$-alkyl, which is substituted in the phenyl ring by phenyl-$C_{0-4}$-alkoxy, which in turn is substituted in the phenyl ring by lower alkyl or lower alkoxy.

9. The method of claim 1, wherein Ar is phenyl, which is substituted by lower alkylenedioxy or is substituted 1 to 3 times by halogen, lower alkyl or lower alkoxy.

10. The method of claim 1, wherein Ar is naphthyl, which is substituted by lower alkylenedioxy or is substituted 1 to 3 times by halogen, lower alkyl or lower alkoxy.

11. The method of claim 1, wherein Ar is indolyl, which is substituted by halogen, lower alkyl or lower alkoxy.

12. A compound corresponding to Formula Id

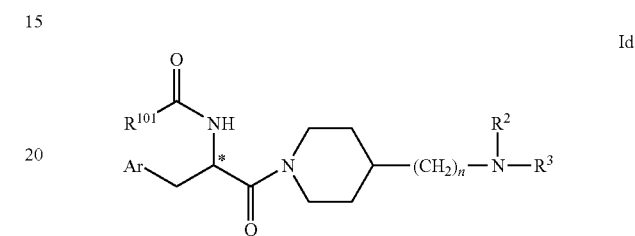

Id wherein
$R^{101}$ is optionally substituted phenyl-$C_{0-4}$-alkyl,
optionally substituted furan,
optionally substituted benzofuran,
optionally substituted thiophene,
optionally substituted benzothiophene,
optionally substituted pyrrole,
optionally substituted $C_{1-6}$-alkyl, or
$C_{3-6}$-cycloalkyl;
$R^2$ is $C_{1-8}$-alkyl,
naphthyl lower alkyl,
fluorenyl lower alkyl, or
optionally substituted phenyl $C_{0-4}$-alkyl;
$R^3$ is hydrogen,
lower alkyl,
naphthyl lower alkyl,
fluorenyl lower alkyl, or
optionally substituted phenyl-$C_{0-4}$-alkyl;
Ar is optionally substituted phenyl,
optionally substituted naphthyl, or
optionally substituted indolyl; and
n is a whole number between 0 and 3,
or a physiologically compatible acid addition salt thereof.

13. The compound of claim 12, wherein $R^{101}$ is phenyl-$C_{0-4}$-alkyl, which is substituted in the phenyl ring by lower alkylenedioxy or is substituted 1 to 3 times by halogen, trifluoromethyl, lower alkyl or lower alkoxy.

14. The compound of claim 12, wherein $R^{101}$ is furan, benzofuran, thiophene, benzothiophene or pyrrole, which is substituted in the heteroaryl ring by halogen, lower alkyl or lower alkoxy.

15. The compound of claim 12, wherein $R^{101}$ is $C_{1-6}$-alkyl, which is substituted by carboxy, hydroxy, oxo, hydroximino, lower alkyloximino, amino, lower alkylamino, di-lower alkylamino or lower alkoxy.

16. The compound of claim 12, wherein $R^2$ is phenyl-$C_{0-4}$-alkyl, which is substituted in the phenyl ring by lower alkylenedioxy or is substituted 1 to 3 times by trifluoromethyl, lower alkyl, di-lower alkylamino, lower alkoxy or phenyl-$C_{0-4}$-alkoxy.

17. The compound of claim 12, wherein $R^2$ is phenyl-$C_{0-4}$-alkyl, which is substituted in the phenyl ring by phenyl- $C_{0-4}$-alkoxy, which in turn is substituted in the phenyl ring by lower alkyl, lower alkoxy or lower alkylenedioxy.

18. The compound of claim 12, wherein $R^3$ is phenyl-$C_{0-4}$-alkyl, which is substituted in the phenyl ring by lower alkylenedioxy or is substituted 1 to 2 times by lower alkyl, di-lower alkylamino, lower alkoxy or phenyl-$C_{0-4}$-alkoxy.

19. The compound of claim 12, wherein $R^3$ is phenyl-$C_{0-4}$-alkyl, which is substituted in the phenyl ring by phenyl-$C_{0-4}$-alkoxy, which is substituted in the phenyl ring by lower alkyl or lower alkoxy.

20. The compound of claim 12, wherein Ar is phenyl, which is substituted by lower alkylenedioxy or is substituted 1 to 3 times by halogen, lower alkyl or lower alkoxy.

21. The compound of claim 12, wherein Ar is naphthyl, which is substituted by lower alkylenedioxy or is substituted 1 to 3 times by halogen, lower alkyl or lower alkoxy.

22. The compound of claim 12, wherein Ar is indolyl, which is substituted by halogen, lower alkyl or lower alkoxy.

23. The compound of claim 12, wherein Ar is substituted indolyl.

24. The compound of claim 12, wherein $R_3$ is hydrogen.

25. The compound of claim 12, wherein * denotes a chiral center in the R configuration.

26. A pharmaceutical composition comprising a pharmaceutically effective amount of a compound according to claim 12, and a pharmaceutical carrier or auxiliary substance.

27. A method of preparing a compound corresponding to Formula Id

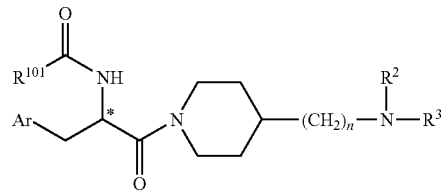

wherein
$R^{101}$ is optionally substituted phenyl-$C_{0-4}$-alkyl,
    optionally substituted furan,
    optionally substituted benzofuran,
    optionally substituted thiophene,
    optionally substituted benzothiophene,
    optionally substituted pyrrole,
    optionally substituted $C_{1-6}$-alkyl, or
    $C_{3-6}$-cycloalkyl;
$R^2$ is $C_{1-8}$-alkyl,
    naphthyl lower alkyl,
    fluorenyl lower alkyl, or
    optionally substituted phenyl-$C_{1-4}$-alkyl;
$R^3$ is hydrogen,
    lower alkyl,
    naphthyl lower alkyl,
    fluorenyl lower alkyl, or
    optionally substituted phenyl-$C_{0-4}$-alkyl;
Ar is optionally substituted phenyl,
    optionally substituted naphthyl, or
    optionally substituted indolyl; and
n is a whole number between 0 and 3, wherein said method comprises:
a) for the preparation of a compound corresponding to Formula Ia'

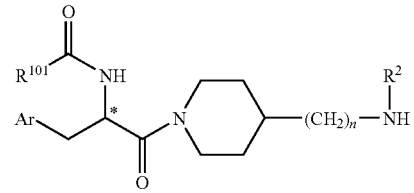

reacting a compound corresponding to Formula II'

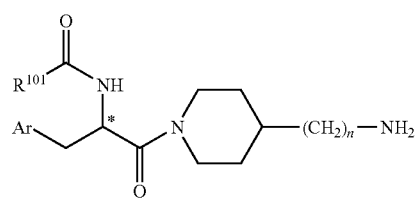

with a compound corresponding to Formula III

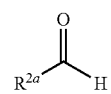

wherein $R^{2a}$ has the same meaning as $R^2$ except that the alkylene chain has one less alkylene group;
in the presence of a reducing agent under conditions of reductive amination; or b) for the preparation of a compound corresponding to Formula Ib'

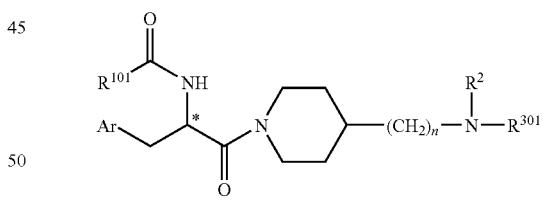

wherein $R^{301}$ has the meaning given above for $R^3$ with the exception of hydrogen, reacting a compound corresponding to Formula Ia' with a compound corresponding to Formula IV

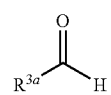

wherein $R^{3a}$ has the same meaning as $R^{301}$ except that the alkylene chain has one less alkylene group;
    in the presence of a reducing agent under conditions of reductive amination.

28. The method of claim 27, further comprising converting a resulting compound corresponding to Formula Id into an acid addition salt thereof or converting an acid addition salt of a compound corresponding to Formula Id into a free base thereof.

29. The method of claim 27, wherein functional groups present in at least one of the compounds corresponding to Formula II', or Formula III or Formula IV, which are reactive under the reaction conditions, are blocked with protective groups.

30. The method of claim 27, wherein functional groups present in at least one compound corresponding to Formula III or Formula IV, which are reactive under the reaction conditions, are blocked with protective groups under conditions of reductive amination and the protective groups are subsequently cleaved.

31. The method of claim 27, wherein $R^{101}$ is phenyl-$C_{0-4}$-alkyl, which is substituted in the phenyl ring by lower alkylenedioxy or is substituted 1 to 3 times by halogen, trifluoromethyl, lower alkyl or lower alkoxy.

32. The method of claim 27, wherein $R^{101}$ is furan, benzofuran, thiophene, benzothiophene or pyrrole, which is substituted in the heteroaryl ring by halogen, lower alkyl or lower alkoxy.

33. The method of claim 27, wherein $R^{101}$ is $C_{1-6}$-alkyl, which is substituted by carboxy, hydroxy, oxo, hydroximino, lower alkyloximino, amino, lower alkylamino, di-lower alkylamino or lower alkoxy.

34. The method of claim 27, wherein $R^2$ is phenyl-C1-4-alkyl, which is substituted in the phenyl ring by lower alkylenedioxy or is substituted 1 to 3 times by trifluoromethyl, lower alkyl, di-lower alkylamino, lower alkoxy or phenyl-$C_{0-4}$-alkoxy.

35. The method of claim 27, wherein $R^2$ is phenyl-C1-4-alkyl, which is substituted in the phenyl ring by phenyl-$C_{0-4}$-alkoxy, which in turn is substituted in the phenyl ring by lower alkyl, lower alkoxy or lower alkylenedioxy.

36. The method of claim 27, wherein $R^3$ is phenyl-$C_{0-4}$-alkyl, which is substituted in the phenyl ring by lower alkylenedioxy or is substituted 1 to 2 times by lower alkyl, di-lower alkylamino, lower alkoxy or phenyl-$C_{0-4}$-alkoxy.

37. The method of claim 27, wherein $R^3$ is phenyl-$C_{0-4}$-alkyl, which is substituted in the phenyl ring by phenyl-$C_{0-4}$-alkoxy, which in turn is substituted in the phenyl ring by lower alkyl or lower alkoxy.

38. The method of claim 27, wherein Ar is phenyl, which is substituted by lower alkylenedioxy or is substituted 1 to 3 times by halogen, lower alkyl or lower alkoxy.

39. The method of claim 27 wherein Ar is naphthyl, which is substituted by lower alkylenedioxy or is substituted 1 to 3 times by halogen, lower alkyl or lower alkoxy.

40. The method of claim 27 wherein Ar is indolyl, which is substituted by halogen, lower alkyl or lower alkoxy.

\* \* \* \* \*